US012714806B2

(12) United States Patent
Parry et al.

(10) Patent No.: US 12,714,806 B2
(45) Date of Patent: Aug. 25, 2026

(54) HEATING ASSEMBLY FOR A VAPOUR GENERATING DEVICE

(71) Applicant: JT International S.A., Geneva (CH)

(72) Inventors: John Parry, Watford (GB); Andrew Robert John Rogan, Forres (GB); Lubos Brvenik, London (GB); Mark Gill, London (GB)

(73) Assignee: JT International S.A., Geneva (CH)

( * ) Notice: Subject to any disclaimer, the term of this patent is extended or adjusted under 35 U.S.C. 154(b) by 684 days.

(21) Appl. No.: 16/957,546

(22) PCT Filed: Dec. 28, 2018

(86) PCT No.: PCT/EP2018/097074
§ 371 (c)(1),
(2) Date: Jun. 24, 2020

(87) PCT Pub. No.: WO2019/129845
PCT Pub. Date: Jul. 4, 2019

(65) Prior Publication Data

US 2021/0068463 A1 Mar. 11, 2021

(30) Foreign Application Priority Data

Dec. 29, 2017 (EP) .................................... 17211201
Dec. 27, 2018 (TW) ................................ 107147308

(51) Int. Cl.
*A24F 40/53* (2020.01)
*A24D 1/20* (2020.01)
(Continued)

(52) U.S. Cl.
CPC ......... *A61M 11/042* (2014.02); *A24F 40/465* (2020.01); *A24F 40/485* (2020.01);
(Continued)

(58) Field of Classification Search
None
See application file for complete search history.

(56) References Cited

U.S. PATENT DOCUMENTS

2012/0048266 A1 3/2012 Alelov
2013/0284192 A1 10/2013 Peleg et al.
(Continued)

FOREIGN PATENT DOCUMENTS

EP 2468116 A1 6/2012
EP 2468117 A1 6/2012
(Continued)

OTHER PUBLICATIONS

International Search Report for Application No. PCT/EP2018/097074 mailed Mar. 29, 2019, 4 pages.
(Continued)

*Primary Examiner* — Philip Y Louie
*Assistant Examiner* — Sonny V Nguyen
(74) *Attorney, Agent, or Firm* — Lerner David LLP

(57) ABSTRACT

A heating assembly for a vapour generating device includes a heating device arranged in use to heat a body, the body including a vaporisable substance, the heating assembly being arranged in use to supply power to the heating device to heat the body, the vaporisable substance volatilising on heating, the quantity of vaporisable substance in the body thereby reducing on heating; a passage arranged in use to allow gas to be drawn over the body; and a controller arranged in use to monitor and store vaporisable substance quantity information of vaporisable substance quantity in the body by determining the amount of previous usage of the body based on stored time the body has been heated for and/or the stored number of times gas has been drawn over the body during heating.

15 Claims, 4 Drawing Sheets

(51) Int. Cl.

| | |
|---|---|
| ***A24F 40/20*** | (2020.01) |
| ***A24F 40/465*** | (2020.01) |
| ***A24F 40/485*** | (2020.01) |
| ***A24F 40/50*** | (2020.01) |
| ***A24F 40/51*** | (2020.01) |
| ***A24F 40/57*** | (2020.01) |
| ***A61M 11/04*** | (2006.01) |
| ***A61M 15/06*** | (2006.01) |
| ***G05B 19/042*** | (2006.01) |

(52) U.S. Cl.

CPC .............. *A24F 40/50* (2020.01); *A24F 40/51* (2020.01); *A24F 40/53* (2020.01); *A24F 40/57* (2020.01); *A61M 15/06* (2013.01); *G05B 19/042* (2013.01); *A24F 40/20* (2020.01); *G05B 2219/2658* (2013.01)

(56) References Cited

U.S. PATENT DOCUMENTS

| | | | | |
|---|---|---|---|---|
| 2013/0319435 | A1 | 12/2013 | Flick | |
| 2014/0014125 | A1 | 1/2014 | Fernando et al. | |
| 2014/0014126 | A1 | 1/2014 | Peleg et al. | |
| 2014/0020693 | A1* | 1/2014 | Cochand | A24F 40/53 131/273 |
| 2014/0096782 | A1* | 4/2014 | Ampolini | A24F 40/60 131/328 |
| 2014/0270727 | A1 | 9/2014 | Ampolini et al. | |
| 2014/0338685 | A1* | 11/2014 | Amir | H05B 1/0244 131/329 |
| 2014/0345606 | A1* | 11/2014 | Talon | A61M 16/0003 128/203.14 |
| 2015/0237916 | A1* | 8/2015 | Farine | A24F 40/53 219/492 |
| 2016/0284197 | A1 | 9/2016 | Liu | |
| 2016/0316821 | A1 | 11/2016 | Liu | |
| 2017/0014582 | A1 | 1/2017 | Skoda | |
| 2017/0055574 | A1 | 3/2017 | Kaufman et al. | |
| 2017/0055584 | A1 | 3/2017 | Blandino et al. | |
| 2018/0060873 | A1 | 3/2018 | Chu | |
| 2018/0104214 | A1* | 4/2018 | Raichman | A24F 40/42 |
| 2018/0220711 | A1 | 8/2018 | Suzuki et al. | |
| 2018/0242644 | A1* | 8/2018 | Bessant | H05B 3/34 |
| 2020/0384220 | A1* | 12/2020 | Bruton | A61M 15/06 |
| 2021/0007402 | A1* | 1/2021 | Qiu | A24F 40/60 |
| 2021/0235770 | A1* | 8/2021 | Uthurry | H05B 1/0297 |
| 2022/0125110 | A1* | 4/2022 | Frake | A24F 40/20 |
| 2025/0031769 | A1* | 1/2025 | Apetrei Birza | A24F 40/53 |

FOREIGN PATENT DOCUMENTS

| | | | |
|---|---|---|---|
| EP | 2609820 | A1 | 7/2013 |
| EP | 3248481 | A1 | 11/2017 |
| EP | 17211201 | A2 | 12/2017 |
| EP | 3275325 | A2 | 1/2018 |
| JP | 2014500017 | A | 1/2014 |
| JP | 2014501105 | A | 1/2014 |
| JP | 2014501107 | A | 1/2014 |
| JP | 2016517270 | A | 6/2016 |
| JP | 2017047014 | A | 3/2017 |
| WO | 9527411 | A1 | 10/1995 |
| WO | 2010073122 | A1 | 7/2010 |
| WO | 2014102091 | A1 | 7/2014 |
| WO | 2014203083 | A2 | 12/2014 |
| WO | 2015082560 | A1 | 6/2015 |
| WO | 2016075436 | A1 | 5/2016 |
| WO | 2016090303 | A1 | 6/2016 |
| WO | 2016166661 | A1 | 10/2016 |
| WO | 2016199065 | A1 | 12/2016 |
| WO | 2016199066 | A1 | 12/2016 |
| WO | 2017029088 | A1 | 2/2017 |
| WO | 2017029089 | A1 | 2/2017 |
| WO | 2017057286 | A1 | 4/2017 |
| WO | 2017137510 | A1 | 8/2017 |
| WO | 2017162687 | A1 | 9/2017 |
| WO | 2017207442 | A1 | 12/2017 |
| WO | 2018050701 | A1 | 3/2018 |
| WO | 2018109611 | A1 | 6/2018 |
| WO | 20180122375 | A1 | 7/2018 |

OTHER PUBLICATIONS

Anonymous, "SN8P2711B User's Manual", of Sonix Technology Co. Ltd., version 2.4,SP5a Printout of https :/ /web.archive.org/web/ 20 170424144613/https :/ /www.sonix.com .twjarticle-en-1005-3116 (Capture of Sonix' website containing the link to SP5, dated Apr. 24, 2017) Nov. 2016, pp. 1-35.

Goniewicz, M. et al., "Nicotine Levels in Electronic Cigarettes" Nicotine & Tobacco Research, Mar. 2012, pp. 158-166, vol. 15, Issue 1.

Notice of Opposition for European Application No. 18833440.3, dated Aug. 31, 2023, pp. 1-35.

Notice of Opposition for European Application No. 18833438.7 dated Sep. 28, 2023. 59 pgs.

* cited by examiner

HEATING ASSEMBLY FOR A VAPOUR GENERATING DEVICE

CROSS-REFERENCE TO RELATED APPLICATIONS

The present application is a national phase entry under 35 U.S.C. § 371 of International Application No. PCT/EP2018/097074, filed Dec. 28, 2018, published in English, which claims priority to European Application No. 17211201.3 filed Dec. 29, 2017 and to Taiwanese Application No. 107147308 filed Dec. 27, 2018, all of the disclosures of which are incorporated herein by reference.

BACKGROUND

The present invention relates to a heating assembly for a vapour generating device and method of heating body.

Devices which heat, rather than burn, a substance to produce a vapour for inhalation have become popular with consumers in recent years.

Such devices can use one of a number of different approaches to provide heat to the substance. One such approach is that of simple provision of a heating element to which electrical power is provided to heat the element, the element in turn heating the substance to generate vapour.

A number of ways of generating vapour exist. This includes using solid or semi-solid vaporisable substances and liquid vaporisable substances. How a vaporisable substance is heated differs depending on whether the substance is solid or semi-solid, or whether the substance is liquid.

Regardless of the type of substance used, the amount of vaporisable substance becomes depleted through use due to the vaporisable substance volatilising on heating and being drawn through the device to a user. This can result in heating being provided when the vaporisable substance is completed depleted, which can cause damage to the device providing the heating, or can cause the body intended to hold the vaporisable substance, such as a cartridge to be burnt.

As the vaporisable substance depletes, the body holding the device can become too hot, i.e. overheat when there is insufficient vaporisable substance present to absorb the heat being provided. This can again cause damage to the body and can occur at any stage during heating, but is particularly noticeable when the vaporisable substance has been depleted from its maximum level.

These issues have previously been addressed by capping the amount of heat provided. However, this causes less reliable generation of vapour making use of the device unsatisfactory to the user.

The present invention seeks to mitigate at least some of the above problems.

SUMMARY OF INVENTION

According to a first aspect, there is provided a heating assembly for a vapour generating device, the heating assembly comprising: a heating device arranged in use to heat a body, the body comprising a vaporisable substance, the heating assembly being arranged in use to supply power to the heating device to heat the body, the vaporisable substance volatilising on heating, the quantity of vaporisable substance in the body thereby reducing on heating; a passage arranged in use to allow gas to be drawn over the body; and a controller arranged in use to monitor and store vaporisable substance quantity information of the quantity of vaporisable substance in the body by determining the amount of previous usage of the body based on stored time the body has been heated for and/or the stored number of times gas has been drawn over the body during heating.

This allows the assembly, and the body, to be used intermittently by a user while the keeping track on the amount of usage the body has undergone by keeping a record of the usage. This allows detection of when the body has reached the end of its useable lifespan, meaning it is possible to avoid heating a body that no longer contains suitable amounts of vaporisable substance, which could cause a risk of heat or burn damage. By the term “gas” we intend to include matter such as air, and air containing vapour, such as vapour from the vaporisable substance, along with other gases and or vapour.

By the term “vaporisable substance” we intend to mean a substance from which vapour is able to be generated. Typically the vapour may be generated by heating the vaporisable substance, but may be generated under other appropriate conditions. The vapour may be in the form of an aerosol, meaning the vaporisable substance may be an aerosol former. The vaporisable substance may itself turn into vapour under appropriate conditions (such as when heated, for example, to above a threshold temperature), or one or more constituents of the vaporisable substance may vaporise (or volatilise) into vapour under appropriate conditions. Further, the vaporisable substance may be a material imbued, soaked or interwoven with a constituent that vaporises under appropriate conditions, or be a product that undergoes a transformation process or produces a material that turns into vapour under appropriate conditions. More detail is provided below in relation to the vaporisable substance.

The controller may conduct any further steps based on the stored vaporisable substance quantity information. Typically, the controller is further arranged in use to set a maximum amount of power suppliable to the heating device based on the stored vaporisable substance quantity information and/or a stored relationship between temperature information determinable from a monitored temperature during heating and an amount of power supplied to the heating device or the profile of power supplied to the heating device. By keeping a record of the quantity of vaporisable substance in the body, the amount of heating amount, also referred to as the heating profile, which corresponds to the level of heat being provided based on the power being provided to the heating device, is able to be adjusted to account for the amount of usage the body has sustained. This allows a suitable amount of heat to be provided to the body minimising the chances of damage being caused by heating since an appropriate amount of heat is provided for the amount of usage the body has undergone.

A maximum amount of power suppliable to the heating device may be set an any suitable level. Typically, the controller is arranged, based on the quantity of vaporisable substance in the body, to set the maximum amount of power suppliable to the heating device lower for a body with less vaporisable substance than a body with more vaporisable substance.

By using a lower heating amount when less vaporisable substance is present, the risk of causing damage is reduced. This is because the heat is absorbed by the vaporisable substance as it volatilises, which prevents the rest of the body becoming too hot. As the quantity of vaporisable substance reduces, this is less able to absorb heat due to the reduced volume available to be volatilised.

Accordingly, by reducing the heating amount, the amount of energy is able to be controlled to keep it close to the same amount for the relative to the quantity of vaporisable substance remaining.

When a previously unused body is provided for heating, the vaporisable substance quantity information for the unused body may be stored in the controller by any suitable means. Typically, the controller is arranged in use to replace stored vaporisable substance quantity information with new vaporisable substance quantity information when the controller determines the body is previously unused.

This reduces the amount of storage space required for storing the vaporisable substance quantity information allowing a smaller storage capacity to be provided, reducing the amount of physical space required for the storage. This also avoids obsolete information being retained making the information storage more efficient by not wasting the storage space available on information that is no longer required.

Stored information may be replaced with new information by writing the new information to where the information is stored and then deleting the previously stored information. Alternatively the stored information may be directly overwritten with the new information to cause the stored information to be simultaneously erased by the new information being written over it.

When a body is to be heated by the heating device, the controller may be arranged to assess whether a body is previously unused when a user seeks to heat a body for the first time in a session, such as at the first puff of the session. This allows the controller to provide power corresponding to a heating amount for a new body. As this will be a higher power amount than with a used body, it allows the new body to be heated up more quickly allowing the assembly to reach full operational ability as quickly as possible. This avoids causing a delay to the user's ability to use the device.

The controller may allow and prohibit heating at any point. Typically, the controller is arranged in use to prohibit heating of the body when the vaporisable substance quantity in the body is below a threshold. This reduces the risk of causing damage when there is too little vaporisable substance left to absorb heat being provided to the body.

The threshold below which the controller is arranged to prohibit heating of the body may be when gas has been drawn over the body between 3 and 30 times or the body has cumulatively been heated for between 5 and 20 minutes, between 10 and 15 minutes, between 5 and 10 minutes, or between 5 and 7 minutes. Having a such a threshold provides the desired protection to the user, assembly and body, especially for devices with a solid vaporisable substance, which are described in more detail below.

The vaporisable substance may be a semi-solid or liquid. Typically, the vaporisable substance is solid when heating is not being applied. Using a solid vaporisable substance allows for greater heat retention and less volatile movements in temperature during a heating sequence.

Heating may be provided any time, and according to any suitable schedule or timing. Typically, the controller is arranged in use to apply heating when gas is being drawn over the body and when no gas is being drawn over the body. This avoids the temperature of the body dropping below a volatilisation temperature of the vaporisable substance. This means no additional time is required to re-heat the vaporisable substance to above its volatilisation temperature when the user wishes to draw gas over the body. This provides a quicker supply of vapour to the user when they seek to draw vapour from the assembly. Additionally, we have found it is more energy efficient to continue heating between draws (as well as during draws) than it is to stop heating during draws and then to start heating again when the next draw occurs. This is again especially the case for devices with a solid vaporisable substance.

Of course, the user may be able to prohibit and enable heating as they choose. This includes the user choosing the assembly to be in an operational state for a period of time, heating being provided as set out above during the period of time the assembly is in an operational state.

Heating may be caused to start and/or stop according to any event or schedule. Typically, the controller is arrange in use to only provide heating after receipt of a first trigger, and/or the controller is arranged in use to stop heating on receipt of a second trigger. This provides control to the user to allow them to put the assembly in an operational state when they expect to be using the assembly and/or when the wish to stop using the assembly. This means heating is only required at certain times, and there is a reduced need for the controller to continuously monitor if heating is required, which reduces the energy usage of the assembly. The first trigger and/or second trigger may be provided by activation of a button, such as a push button, by a user. The first trigger may be provided by a cover of a heating compartment being opened by a user. The second trigger may be provided by the cover of the hearing compartment closing. The cover may close automatically due to the cover typically having a bias to a closed position and being stopped from closing in use due to the presence of a body in the heating compartment. The second trigger may be a predetermined period, e.g. 1 minute, 3 minutes or 5 minutes, of time elapsing since a user drew vapour from the assembly, such as by actively drawing air through a mouthpiece.

Additionally, or alternatively, the device may further comprise a temperature sensor arranged in use to monitor a temperature relating to heating at the body. This allows direct monitoring of the body to allow temperature to be known and taken account of by the assembly and controller.

The temperature sensor may be a thermistor or a thermocouple. For example, the temperature sensor may be a resistance temperature detector, such as a resistance temperature detector, which may use a platinum resistor as a sensing element. The platinum resistor may be a platinum film (e.g. a thin film) on a ceramics substrate, which may be passivated by glass coating. The temperature sensor may for example be a PT100 from Measurement Specialties, Inc of the PTF family of sensors.

When a temperature sensor is present, the controller may be arranged in use to receive temperature information from the temperature sensor and to stop heating if a temperature of the body exceeds a predetermined threshold. This allows the risk of overheating of the body to be reduced thereby improving user safety and further reducing the risk of the assembly or body becoming damaged by excess heat.

Also, or alternatively, when a temperature sensor is present, the controller may determine a body is previously unused based on data being provided to the controller or any other means. Typically, the controller may be arranged in use to determine the body is previously unused based on a stored relationship between temperature information determinable from a monitored temperature during heating, age of a body and the amount of power supplied to the heating device or the profile of power supplied to the heating device. This allows the age of the body to be derived from the relationship. This has the benefit of allowing suitable heating to be provided to the unused body, for example avoiding slower heating when a non-optimal amount of power is being provided. This also allows a suitable remaining heating period and/or puff count to be stored to allow for correct heating to be applied over the usage period of the body by a user.

By "profile of power supplied to the heating device", it is intended to mean the manner in which the power is provided to the heating device, for example taking into account the rate of change of the power supplied, and/or the time amount time over which power is provided to the heating device. For example, the amount of power, or rate of power delivery may be the same, but the power may be supplied over a period of 1 second or over a period of 3 seconds, which may resulting in the body being heated to a different temperature.

The assembly may be arranged to obtain, in use, temperature information. The temperature information may be generated or determined by a controller of the heating assembly, a temperature sensor or by an external processing unit. The temperature information may be generated or determined by processing a monitored temperature, such as by recording a monitored temperature over a predetermined time period and analysing the recorded monitored temperature for trends including, for example, rate of change, increase, decrease, variation or a number of other factors. The power usage of the heating device and/or power supplied to the heating device may also be monitored and/or recorded and/or determined by the heating device, the controller or the external processing unit.

The temperature information may include the monitored temperature itself or any other pertinent information able to be obtained from monitoring the temperature. Typically, the temperature information includes a rate of change of the monitored temperature. The rate of change of temperature allows the speed at which the temperature of the body is increasing to be known. We have found that this is a useful piece of information for ascertaining the age of the body due to differences in how quickly a body heats up as moisture levels in the body decrease through usage.

Additionally or alternatively, temperature information may include a surface temperature of the body. Having the surface temperature of the body available is also useful. This is because we have found that different body types warm to different temperatures for the same amount of power usage. As such, this assists with identifying the body type. Additionally, this assists with determining age of a body because, for a particular amount of power usage, we have found that a more used body reaches a higher (surface) temperature than a less used body.

One example of the monitored temperature may also be a surface temperature of the body.

Once the temperature information has been obtained, at least one condition may be determinable from the temperature information and the amount of power supplied to the heating device in the first power supply mode based on the relationship held in the memory.

This allows the controller to decide on the next step of how to heat as soon as possible, e.g. the heat profiling in the later part of the first mode and/or the second mode can be determined based on the detected condition. Further in the first power supply mode, a large amount of power is supplied in a short period. As such, it is beneficial for controller to determine the at least one condition more easily and accurately in a short period.

Additionally, it may be possible to determine useful information from the rate of increase of detected temperature during the first power supply mode while the body is heating up towards the target temperature. For example, if the body contains a significant amount of water, for example greater than 5%, then it may be possible to detect a reduction in the rate of increase of the (surface) temperature of the body at about 100° C. as the water present in the body starts to vaporise at about this temperature, causing energy to be consumed in vaporising the water rather than it increasing its temperature. The amount of water contained in the body may be an indicator of the amount of time that the body has been stored in an ambient environment having significant humidity without the benefit of protective packaging. Such water content may also be detrimental to the quality of vapour produced by the assembly. It may therefore be beneficial to cease heating the body and advise the user to dispose of the body and replace it with a new, fresh (for example, unused) body, or else to advise the user to wait until commencing vapour and to continue to heat the body at a reduced temperature (sufficient to vaporise all or most of the excess water) until most of the (excess) water has been vaporised and then to heat the body to the operating temperature, etc. Other constituents may also be detectable in this way, or other characteristics of the body may be determinable based on the particular temperature ramp up profile.

The controller may determine a body is previously unused at any stage. Typically however, the controller is arranged in use to determine if the body is a previously unused body on detection of a body being placed for heating by the heating device. This allows a body to be determined as being unused as soon as possible so that the appropriate heating conditions can be applied from as soon as the body is to be used. Of course, typically heating is only applied when the assembly is in a heating state, such as when a user has indicated heating is to be provided, such as by providing the first trigger.

Further, detection of a body being placed for heating by the heating device may be determined by detection of the body being placed in the appropriate location for heating, such as in a heating compartment of the heating device. The detection may be achieved using a sensor, or switch, that is arranged in use to operate, or send a signal to the controller, when a body is removed and/or placed in the appropriate location. This may for example be achieved through use of a switch on a mouthpiece or a lid of the heating chamber, the switch sending a signal to the controller when the mouthpiece or the lid is moved to allow placement of a body in a heating compartment. Namely the sensor or switch can be on the part of the heating device with which the user is able to interact when the user replaces a body. The operating or sending of a signal to the controller when a body is removed and/or placed in the appropriate location may provide the first trigger.

Typically, the vaporisable substance quantity information may comprise remaining heating time available and/or remaining number of times gas is able to be drawn over the body during heating. Additionally, the stored vaporisable substance quantity information may be used as vaporisable substance quantity information for next heating session if the controller determines the body is a used body in said next heating session. This allows previously held data on a body to be used, reducing the analysis that needs to be conducted on a body to ascertain the remaining lifespan of the body.

The vaporisable substance quantity information may be stored in any location. Typically, the controller is arranged to store vaporisable substance quantity information in a memory. The memory may be located within the heating assembly. Alternatively the memory may be located outside of the heating assembly. Should this be the case, the assembly may have a memory accessor arranged in use to access the memory. Storing the information in a memory allows the controller to not store information about the body within the controller or assembly itself, allowing more storage space with the controller to be dedicated to operating the controller. This either allows a controller with smaller storage space to be used thereby making the controller physically smaller, and/or allows the controller to perform a greater number of functions by instead dedicating storage space to functional aspects.

The assembly of this aspect may relate to devices using solid vaporisable substance, hereafter referred to as a "solid-vapour device", instead of devices using liquid vaporisable substance, hereafter referred to as a "liquid-vapour device". Solid vapour devices produce vapour by heating tobacco, tobacco products or other such solid vaporisable substances, whereas liquid-vapour devices produce vapour by heating a liquid.

In both types of device, to use the device, a user draws vapour from the device. This is referred to as a "puff" as the device typically provides a puff of vapour from a mouthpiece. To produce vapour for a puff, the vaporisable substance is heated. This is common to solid-vapour devices and liquid-vapour devices.

Users typically use a device for a time period of their choosing over which they draw several puffs from the device regardless of the type of the device. This period of use of the device producing one or more puffs is referred to as a "session". Each session therefore has a first puff at the start of the session and generally has further puffs.

The energy requirements to produce the first puff are different for solid-vapour devices than for liquid-vapour devices.

One of assumption is that due to an ability for liquid vaporisable substance to move towards a heating device during use such that only a small amount of liquid needs to be vaporised (ideally just enough for one puff), but this not being possible for solid vaporisable substances, a heating device in a solid-vapour device needs to provide more heat to be able to heat a much larger amount of the solid vaporisable substance (e.g. the whole portion) which would also typically tend to be further from the heating device. This of course requires more energy and time as the heat must be transmitted further from the heating device. As such, due to the smaller quantity to heat and the amount of heating needing to be provided. This means that in such solid-vapour devices, in general, more power and time is required than for a liquid-vapour device for the first vapour to be output during a puff when the vaporisable substance is heated from the same temperature (normally ambient temperature). As a demonstration of this, in general, solid-vapor devices currently need several seconds or more after starting heating before vapour is generated, whereas liquid-vapour devices can generate vapour almost at the same time as starting to provide heating.

In general, in liquid-vapour devices, power is only supplied to a heating device when a user actively draws a puff from the device. On the other hand we have found that in solid-vapour devices, power may be supplied to a heating device (in the case of the assembly of the first aspect, to the heating device) at any time after the assembly is switched on. By providing heating in such a manner, this means that after a vaporisable substance has reached a temperature that causes the substance to vaporise, i.e. a vaporisation temperature or target operational temperature, for example, after a first power supply mode, vapour continues to be generated regardless of whether a user is drawing a puff. This also allows a user to actively draw on the mouthpiece and to be provided with vapour at any time during a session, for example, during a second power supply mode. This is in line with a conventional cigarette.

We have found that by providing continuous heating during a session, an energy saving is achieved. This is because it generally requires more energy to re-heat a solid vaporisable substance that has been allowed to cool below the target operational temperature than it does to maintain the solid vaporisable substance at the target operational temperature. Further, by maintaining the temperature for later puffs, a user can draw vapour from the device in a puff at any time without waiting as they may need to do for the first puff.

Accordingly, in relation to the first aspect typically, the heating device is arranged in use to heat the vaporisable substance during a period where a user is drawing air through a mouthpiece of the assembly. In this case by "period" it is intended to mean a session, meaning that heating is being provided over the whole of the length of the session. In some circumstances however, "period" could be intended to mean only during the time when a user is actively drawing air/gas/vapour/aerosol through the mouthpiece.

Since the user is able to choose when to actively draw on the device, the period between draws in a session is likely not to be regular. During a session, if the gap between draws is too long, the amount of energy used by a solid-vapour device maintaining the vaporisable substance at the target operational temperature will be higher than allowing the vaporisable substance to cool and be re-heated. As long as the gap between occasions when the user actively draws on the device is not too long, the energy saving advantage set out above is achieved. To avoid the efficiency gains being lost, the session in a solid-vapour device may "time out" by stopping heating after a predetermined period, requiring a session to be re-started when the user next wishes to draw on the device.

Accordingly, in relation to the first aspect, the heating device may be arranged in use to end heating of the vaporisable substance if the period since the last draw of air through the mouthpiece by a user is greater than a predetermined period. Air passage through the mouthpiece by a user may be detectable by a sensor in the device, such as a temperature sensor, pressure sensor (such as a pressure-based puff sensor) or flow sensor. For example, the temperature sensor may detect temperature fluctuations when a user causes passage of air through the mouthpiece (and heating compartment).

The heating assembly may be an induction heating assembly, the heating device may be an induction heating device, and the body may further comprise an induction heatable susceptor, the induction heating device being arranged to heat, in use, the induction heatable susceptor of the body, the heating assembly being arranged to supply, in use, power to the induction heating device to heat the induction heatable susceptor; the temperature sensor being arranged to monitor, in use, a temperature related to heat generated from the susceptor, temperature information related to heat generated from the susceptor being determinable from the monitored temperature.

By using induction heating, the heat is generated within the body, and only when the susceptor is present. As such, the heating is more efficient because it is generated within the body instead of having to be transferred to the body, for example, by conduction away from the heating device (which would also cause heating of components other than the body). Additionally, heating by induction improves safety because no heat will be generated without there being a suitable body located in the heating compartment to heat. This also avoids heating being applied needlessly or by accident when no suitable body is present in the heating compartment. The heating assembly is arranged to generate vapour from solid vapour generating material within 5 seconds, preferably 3 seconds after start heating (i.e. within 3 seconds). Intermittent use of the device and induction heating has a synergistic effect. This is that the induction heating generates vapour quickly compared to other heating systems such as resistive heating, meaning the user does not have to wait before each occasion heating re-starts. The combination of using solid vapour generating material and quick heating thus achieves saving energy, effective use of the solid vapor generating material and limiting waiting time for the user, meaning they have more comfortable use of the assembly at the same time.

The susceptor may comprise one or more, but not limited, of aluminium, iron, nickel, stainless steel and alloys thereof, e.g. nickel chromium. With the application of an electromagnetic field in its vicinity, the susceptor may generate heat due to eddy currents and magnetic hysteresis losses resulting in a conversion of energy from electromagnetic to heat.

When using induction heating, the assembly may include a fluctuating electromagnetic field generator, for example in the form of an induction heating coil and associated driving circuitry and a power source, arranged to operate in use to generate a fluctuating electromagnetic field having a magnetic flux density of between approximately 0.5 Tesla (T) and approximately 2.0 T at the point of highest concentration.

The power source and circuitry may advantageously be configured to operate at a high frequency whereby it may drive an induction heating coil of the heating device at a similarly high frequency. Preferably, the power source and circuitry may be configured to operate at a frequency of between approximately 80 kHz and 500 kHz, preferably approximately 150 kHz and 250 kHz, more preferably approximately 200 kHz. Preferably, in embodiments including an induction heating coil, the power source drives the induction coil at the same frequency (i.e. between approximately 80 kHz and 500 kHz, preferably approximately 150 kHz and 250 kHz, more preferably approximately 200 kHz).

Whilst the induction coil, which is one form the induction heating device may take, may comprise any suitable material, typically the induction coil may comprise a Litz wire or a Litz cable.

The use of induction heating provides several technical advantages in embodiments in which it is used. For example, in embodiments which require a body to include susceptors (as discussed above) in order to be heated by the device, if a body is inserted into the device which does not include a susceptor (i.e. if an unsuitable body is inserted into the device—e.g. by mistake) then it can readily be determined that no suitable body is present in the device based on the relationship between power applied to the heating device and the temperature information relating to heating at the body.

Thus, in some embodiments, a suitable body may be provided with a susceptor or susceptors having a predetermined resonant frequency. In such a case it may be possible to distinguish between suitable and unsuitable bodies based on monitoring and detecting the relationships between power applied to the heating device and temperature information when the fluctuating magnetic field generator generates fluctuating magnetic fields at the predetermined resonant frequency. In particular, in such a case, there would be an expected range of rates at which the temperature should increase to identify a suitable body for heating. In particular, too slow a rate of heating would indicate that the body did not include a suitable substrate, whereas heating too quickly could indicate either that an unsuitable susceptor is included or that the body is too old or has already been heated and is thus depleted of humectant, etc.

Any determination of a remaining heating amount or a remaining number of times gas is able to be drawn over the body during heating may be based on a detected rate of increase of temperature. Typically instead however, a remaining heating amount for the body is based on stored vaporisable substance quantity information. This may be following a determination of whether the body is used or unused based on information stored in the assembly allowing less power to be used to carry out such a determination.

The heating device may have a first power supply mode and a second power supply mode, wherein in use the heating device is arranged to monitor and store vaporisable substance quantity information before entering the second power supply mode, such as when in the first power supply mode. At this stage, the temperature of the body may be increased to a predetermined temperature and/or heating may be provided over a predetermined period during the application of a predetermined power level to the heating device. Any monitoring and heating may be carried out in response to a trigger, such as in response to the first trigger described herein.

When in the second power supply mode, the heating device may be configured to maintain the body at a predetermined temperature and/or to generated heat based on a predetermined power level, such as due to the maximum amount of power suppliable to the heating device being set. This application of different power supply modes and monitoring allows a determination of whether the body is used or unused to be carried out before the heating device maintains the body at a predetermined temperature. This means a use level can be determined and the heat to the appropriate temperature can be provided to the body reducing the risk of damaging the body or assembly. When in the first power supply mode, the heating device may be arranged to increase the temperature of the body.

During the period the heating device is in the second power supply mode, vaporisable substance quantity information may be monitored in order to track (e.g. record) the amount of usage of the body. This monitoring may differ from the monitoring carried out when the heating device is in the first power supply mode. This is because the monitoring conducted when in the second power supply mode may be monitoring of (stored) vaporisable substance quantity information to allow a comparison to be carried out against any on-going usage of the assembly that is causing the body to be heated. In other words, the monitoring when the heating device is in the second power supply mode may be monitoring to record the reduction in vaporisable substance in the body during a session compared to monitoring to ascertain the quantity of vaporisable substance in the body at the start of the session as may be carried out when the heating device is in the first power supply mode in line with the process set out above. Of course, other steps may also be carried out when the heating device is in either power supply mode.

Accordingly, the first power supply mode may be arranged to be applied, in use, when heating the body, and the second power supply mode may be arranged to be applied, in use, after the first power supply mode is applied, to maintain the body at a temperature within a predetermined temperature range, preferably when in the first power supply mode, the heating assembly is arranged to provide at least 80 percent (%) of full power to the heating device. This allows the at least one condition of the body to be detected based on power usage and temperature information obtained whilst the assembly is operating in one mode, but also provides a further mode where the processing corresponding to determining the at least one condition of the body need not be carried out. Since carrying out the determination requires processing to be conducted, which uses power, having a power supply mode that does not involve the determination thereby reduces the power usage attributable to said determination.

After determination of vaporisable substance quantity information of the body, the controller may be further arranged in use, based on the determined vaporisable substance quantity information, to perform of one of: prohibit heating by the heating device, update the vaporisable substance quantity information and initiate heating by the heating device, or initiate heating by the heating device. Typically, this may be achieved by the controller being adapted in use to determine if the body is a body unsuitable for use with the assembly, is a suitable used body or a suitable unused body, wherein after determination if the body is an unsuitable body, is a suitable unused body or is a suitable used body, the controller is further arranged in use, based on said determination, to perform of one of: if the body is determined as an unsuitable body, prohibit heating by the heating device, if the body is determined as a suitable unused body, initiate heating by the heating device and replace stored vaporisable substance quantity information with new vaporisable substance quantity information, or if the body is determined as a suitable used body, initiate heating by the heating device based on the stored vaporisable substance quantity information.

This allows the heating assembly to take appropriate action based on the anticipated amount of remaining vaporisable substance in the body, thereby reducing the risk of the device or body becoming damaged by inappropriate action taking place for the amount of vaporisable substance remaining in the body. Additionally, this process may be carried out when the heating device is in the first power supply mode, and may be at least part of monitoring that may be carried.

By "a body unsuitable for use with the assembly" it is intended to mean a body that the assembly was not designed to be compatible with. This may be a body with particular types of vaporisable substance, or made from particular materials, for example.

The body may be determined as being used or unused as defined herein, as well as a determination being carried out as to whether the body is a suitable or unsuitable body. Of course, the determination as to whether the body is suitable or unsuitable may be determinable separately from whether the body is used or unused, or may be determinable at the same time.

In this instance, "prohibit heating" may mean that heating that is already taking place is stopped, or that heating is not started when it would otherwise have been started following the determination being carried out (i.e. if the result of the determination had been different).

According to a second aspect, there is provided a method of heating a body, the body comprising a vaporisable substance, the vaporisable substance volatilising on heating, the method comprising: determining with a controller the amount of previous usage of the body based on stored time the body has been heated for and/or the stored number of times gas has been drawn over the body during heating; setting with the controller a maximum amount of power suppliable to the heating device based on the stored vaporisable substance quantity information; and heating the body with a heating device supplied with power to heat the body by providing the set maximum amount of power.

As with the first aspect, this allows a suitable amount of heat to be provided to the body minimising the chances of damage being caused by heating since an appropriate amount of heat is provided for the amount of usage the body has undergone. By the term "volatilising", we intend to mean that producing vapour, or to produce vapour.

The method of the second aspect may also include that on starting heating, providing a predetermined power level for a predetermined time period and monitoring the rate of increase of temperature during said time period, the monitored rate being the temperature information, and setting a remaining heating amount for the body based on the age of the body determined from the relationship held in the memory.

By "heating amount" it is intended to mean the remaining amount the body can be heated before the body is considered to have expired or have been used to its full extent. A body is considered to have expired or to have been used to its full extent when a predetermined amount of vaporisable substance is left in the body, such as zero. The heating amount may be measured in an amount of time remaining for which the body can be heated under a pre-determined condition, or the number of draws of gas over the cartridge/body, also referred to as "puffs", remaining before heating of the body will cause the body to expire.

Determining the remaining heating amount allows heating to be stopped before further heating becomes dangerous or would cause the body to burn or become damaged. This reduces the risk to the user and reduces the likelihood of damaging the device holding the body by overuse of the body.

Once the remaining heating amount is determined, this amount may be stored in the memory and/or a controller and preferably the remaining heating amount is monitored while the user is causing the device to be used (e.g. by heating) and the controller and/or memory may determine when the remaining heating amount has elapsed. This reduces the chances of the body being over used and becoming burnt or causing damage.

The monitored rate may also be used to determine if the body is a body compatible with the heating device based on the relationship between the temperature information, the amount of power supplied to the heating device and at least one condition, when the body is determined as being compatible heating continues, and when the body is determined as being incompatible, heating is stopped. This again reduces the risk of the body being heated from causing damage and harming the user through unsuitable heating.

When heating is stopped due to an incompatible body, an indication may be provided to the user. This alerts the user to the need to change the body. Heating may also be stopped when the remaining heating amount is determined to have been used.

Heating of the body may be started and/or stopped by a trigger. This allows greater user control of the heating, which may prolong the lifespan of the body. This trigger may be the first trigger or second trigger as set out above.

According to a third aspect, there is provided a vapour generating device comprising: a heating assembly according to the first aspect; a body containing a vaporisable substance, the body being heatable by the heating assembly; and an air inlet and air outlet providing a passage therebetween arranged in use to allow gas to pass over the body during heating to provide air to the heating compartment.

The body (which is also referred to as a cartridge) may include any suitable material. Typically, the cartridge includes humectant or tobacco containing moisture, and preferably the cartridge is a single use cartridge arranged to expire, in use, on consumption of a predetermined amount of at least one constituent of the cartridge. Such a humectant or tobacco may be the vaporisable substance.

The vaporisable substance would be any type of solid or semi-solid material. Example types of vapour generating solids include powder, granules, pellets, shreds, strands, porous material or sheets. The substance may comprise plant derived material and in particular, the substance may comprise tobacco.

Preferably, the vaporisable substance may comprise an aerosol-former. Examples of aerosol-formers include polyhydric alcohols and mixtures thereof such as glycerine or propylene glycol. Typically, the vaporisable substance may comprise an aerosol-former content of between approximately 5% and approximately 50% on a dry weight basis. Preferably, the vaporisable substance may comprise an aerosol-former content of approximately 15% on a dry weight basis.

Examples of solid materials which contain a liquid aerosol former which are suitable for forming the body in embodiments of this invention include tobacco rods comprising sheets of reconstituted tobacco paper impregnated with humectant, typically up to amounts of about 20% humectant by weight, the humectant typically being glycerol or a mixture of glycerol and propylene glycol, finely ground tobacco particles with humectant added to form a paste, or a tobacco mousse also formed from finely ground tobacco particles mixed with humectant, but typically also including a gel forming agent and with levels of humectant up to about 40% by weight (preferably between 20% and 40%) such as described in pending patent application WO 2018/0122375. Using bodies such as mousse with high levels of humectant (whilst still being sufficiently dry around the surface to prevent staining surfaces which they may contact) makes certain embodiments advantageous because it is possible to detect the type of such bodies without the need to provide some form of paper wrapping or packing for the body to render its type identifiable by means of a printed indication, thus being environmentally friendly in terms of minimising excess packaging matter. Additionally, such bodies having a high weight of humectant are well suited to having their state of use identified by measuring the rate of increase of their temperature under heating as this can vary considerably as the humectant is used up, especially for bodies such as mousse where the humectant is almost completely used up during vaping (going from about 40% by weight to close to zero % by weight after a full vaping session).

Upon heating, the vaporisable substance may release volatile compounds. The volatile compounds may include nicotine or flavour compounds such as tobacco flavouring.

The body may be a capsule which includes in use a vaporisable substance inside an air permeable shell. The air permeable material may be a material which is electrically insulating and non-magnetic. The material may have a high air permeability to allow air to flow through the material with a resistance to high temperatures. Examples of suitable air permeable materials include cellulose fibres, paper, cotton and silk. The air permeable material may also act as a filter. Alternatively, the body may be a vaporisable substance wrapped in paper. Alternatively, the body may be a vaporisable substance held inside a material that is not air permeable, but which comprises appropriate perforation or openings to allow air flow. Alternatively, the body may be the vaporisable substance itself. The body may be formed substantially in the shape of a stick.

According to a fourth aspect of the present invention, there is provided a body or cartridge for use with any of the preceding aspects, comprising a vaporisable substance and adapted such that at least one condition including an age of the body or capsule, a type of the body or capsule or the presence of the body or capsule, can be determined in dependence upon a relationship between power supplied to a heating device for heating the body or capsule and temperature information related to heating at the body or capsule. Preferably, the adaptation may include providing a body having a percentage of vaporizable liquid (preferably of humectant such as propylene glycol and/or glycerine, but possibly additionally including other vaporizable liquids such as water or ethanol, etc.) which is greater than 20 wt % or 10 wt % (100 wt % is equal to the total weight of the liquid and the vaporisable substance, such as tobacco, humectant and/or plant derived material) when fresh or "young" which reduces by at least 4 wt % when the body or capsule has been heated over one session or left after removing from a packaging associated with the body or capsule for more than a predetermined period of time (of preferably at least 3 months) in predetermined environmental conditions. Most preferably, the vaporizable liquid reduces by at least 7% when heated over one session.

The adaptation to the body or capsule for the purpose of the fourth aspect of the present invention may include providing a susceptor in the body or capsule which has a heating efficiency which depends upon the frequency of an energising fluctuating magnetic field, such that it has a maximum heating efficiency at a first predetermined resonant frequency and falls to below a predetermined heating efficiency threshold of 50% of the maximum heating efficiency either side of a frequency range.

According to a fifth aspect of the present invention, there is provided a set of bodies of cartridges according to the fourth aspect of the present invention, packaged within a packaging adapted to prevent the percentage of vaporizable liquid from falling less than 3 wt % for a predetermined period of time preferably of at least one year, until the packaging is opened (e.g. by a consumer).

BRIEF DESCRIPTION OF FIGURES

An example heating assembly and example processes are described in detail below, with reference to the accompanying figures, in which.

DETAILED DESCRIPTION

We now describe an example of a vapour generating device, including a description of an example induction heating assembly, example induction heatable cartridges and example susceptors. While only heating by induction is described below, other forms of heating, such as resistive heating, exist and are able to be applied in the example vapour generating device instead of heating by induction.

Figure 1:
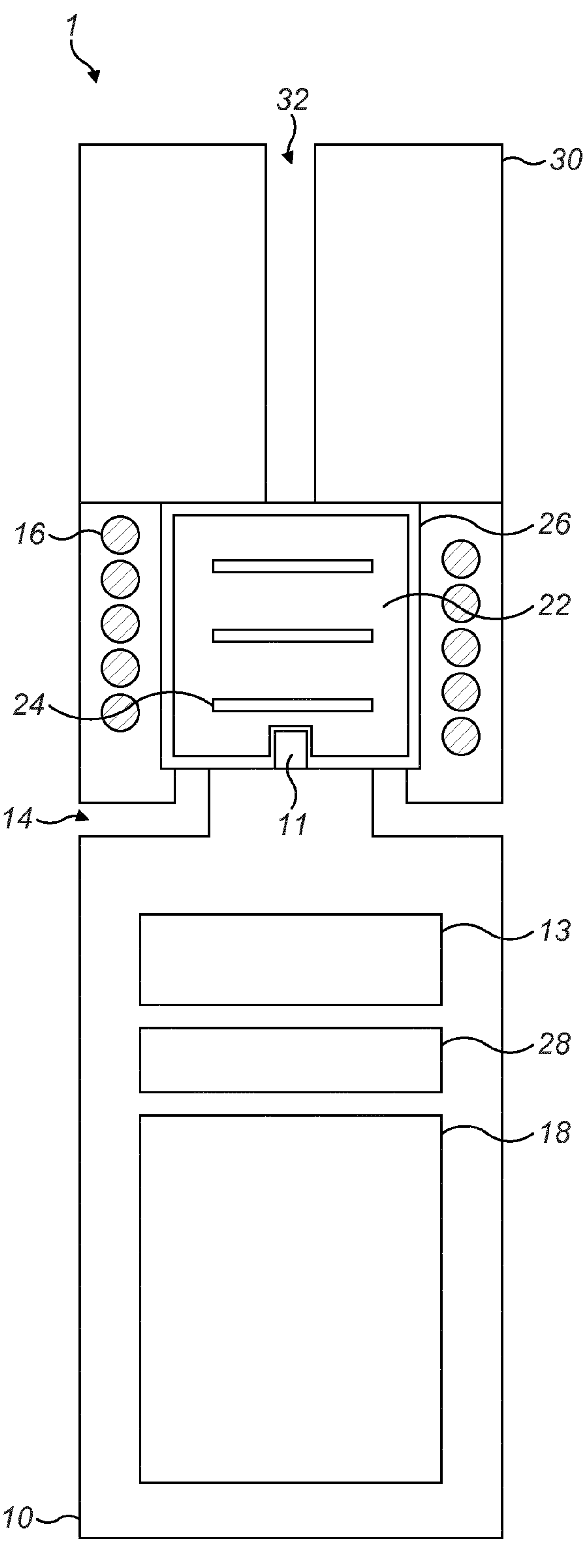
FIG. 1 shows a schematic view of an example vapour generating device.
Figure 2:
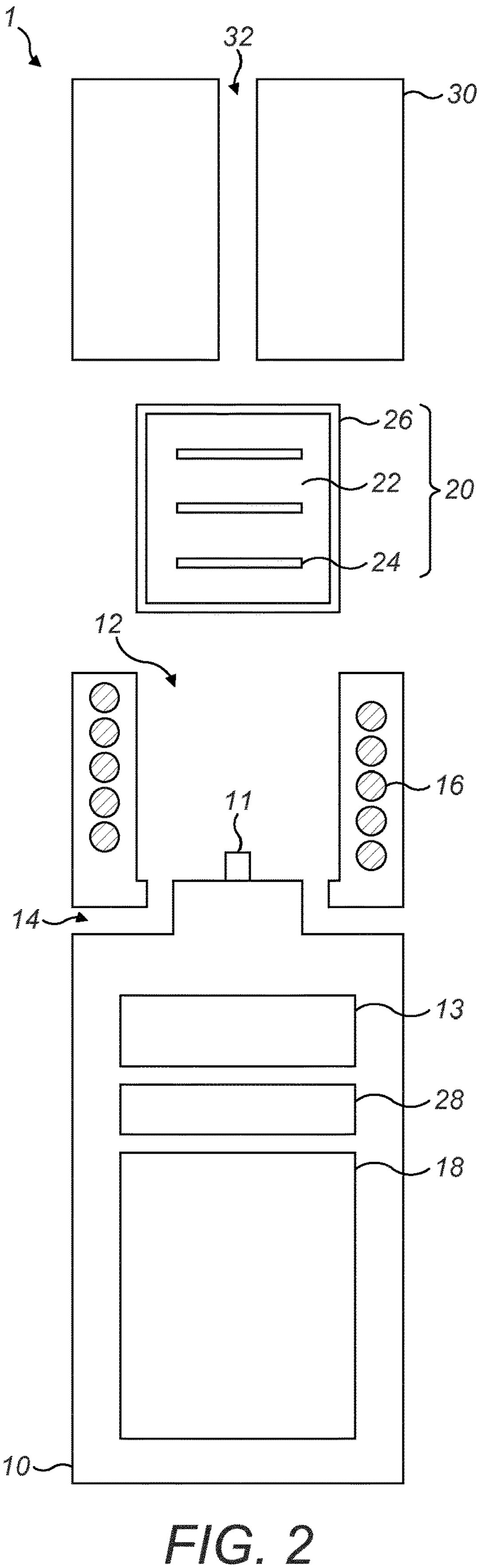
FIG. 2 shows an exploded view of the vapour generating device according to the example shown in FIG. 1.

Referring now to FIG. 1 and FIG. 2, an example vapour generating device is generally illustrated at 1 in an assembled configuration in FIG. 1 and an unassembled configuration in FIG. 2.

The example vapour generating device 1 is a hand held device (by which we intend to mean a device that a user is able to hold and support un-aided in a single hand), which has an induction heating assembly 10, an induction heatable cartridge 20 and a mouthpiece 30. Vapour is released by the cartridge when it is heated. Accordingly, vapour is generated by using the induction heating assembly to heat the induction heatable cartridge. The vapour is then able to be inhaled by a user at the mouthpiece.

In this example, a user inhales the vapour by drawing air into the device 1 from the surrounding environment, through or around (each corresponding to, for example, generally over) the induction heatable cartridge 20 and out of the mouthpiece 30 when the cartridge is heated. This is achieved by the cartridge being located in a heating compartment 12 defined by a portion of the induction heating assembly 10, and the compartment being in gaseous connection with an air inlet 14 formed in the assembly and an air outlet 32 in the mouthpiece when the device is assembled. This establishes a passage through the assembly and allows air to be drawn through the device by application of negative pressure, which is usually created by a user drawing air from the air outlet.

The cartridge 20 is a body which includes a vaporisable substance 22 and an induction heatable susceptor 24. In this example the vaporisable substance includes one or more of tobacco, humectant, glycerine and propylene glycol. The vaporisable substance is also solid. The susceptor includes a plurality of plates that are electrically conducting. In this example, the cartridge also has a layer or membrane 26 to contain the vaporisable substance and susceptor, with the layer or membrane being air permeable. In other examples, the membrane is not present.

As noted above, the induction heating assembly 10 is used to heat the cartridge 20. The assembly includes an induction heating device, in the form of an induction coil 16 and a power source 18. The power source and the induction coil are electrically connected such that electrical power may be selectively transmitted between the two components.

In this example, the induction coil 16 is substantially cylindrical such that the form of the induction heating assembly 10 is also substantially cylindrical. The heating compartment 12 is defined radially inward of the induction coil with a base at an axial end of the induction coil and side walls around a radially inner side of the induction coil. The heating compartment is open at an opposing axial end of the induction coil to the base. When the vapour generating device 1 is assembled, the opening is covered by the mouthpiece 30 with an opening to the air outlet 32 being located at the opening of the heating compartment. In the example shown in the figures, the air inlet 14 has an opening into the heating compartment at the base of the heating compartment.

A temperature sensor 11 is located at the base of the heating compartment 12. Accordingly, the temperature sensor is located within the heating compartment at the same axial end of the induction coil 16 as the base of the heating compartment. This means that when a cartridge 20 is located in the heating compartment and when the vapour generating device 1 is assembled (in other words when the vapour generating device is in use or ready for use) the cartridge is deformed around temperature sensor. This is because, in this example, the temperature sensor does not pierce the membrane 26 of the cartridge due to its size and shape.

The temperature sensor 11 is electrically connected to a controller 13 located within the induction heating assembly 10. The controller is also electrically connected to the induction coil 16 and the power source 18, and is adapted in use to control operation of the induction coil and the temperature sensor by determining when each is to be supplied with power from the power source.

Figure 3:
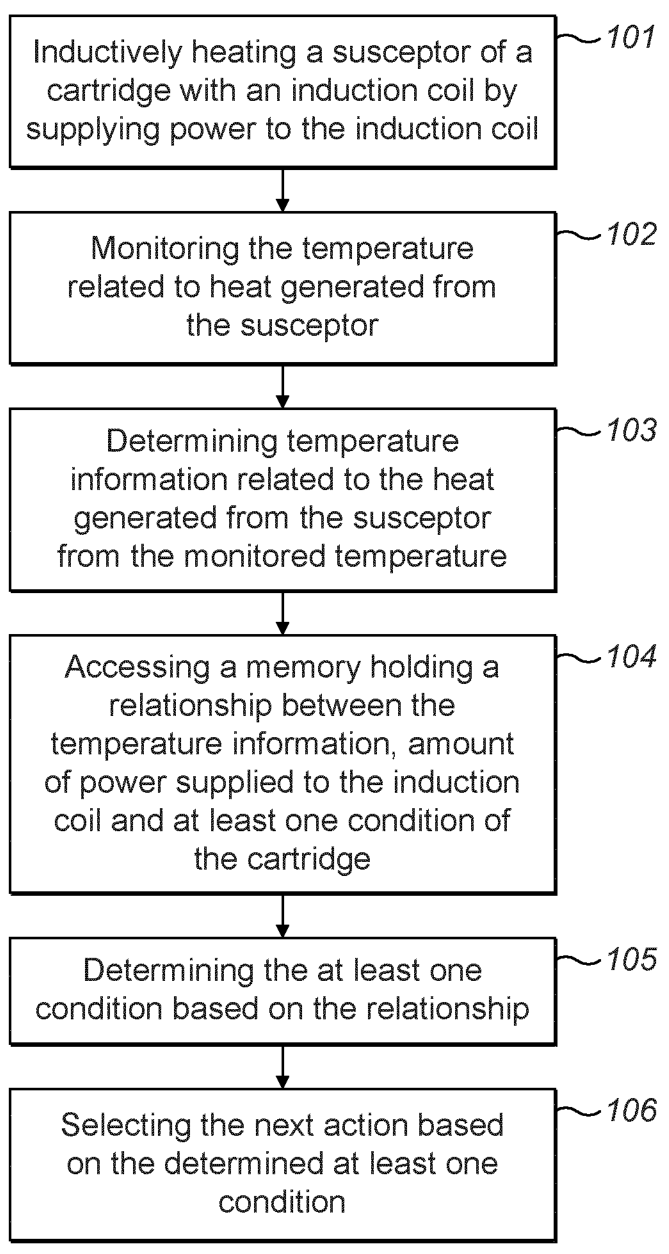
FIG. 3 shows a flow diagram of an example process.

An example process as shown in FIG. 3 is now described. As mentioned above, in order for vapour to be produced, the cartridge 20 is heated, step 101. This causes volatilisation of the vaporisable substance.

Heating is achieved by a direct electrical current supplied by the power source 18 being converted to an alternating current (AC) which is in turn fed to the induction coil 16. The current flows through the induction coil causing a controlled EM field to be generated in a region near the coil. The EM field generated provides a source for an external susceptor (in this case the susceptor plates of the cartridge) to absorb the EM energy and convert it to heat, thereby achieving induction heating.

In more detail, by power being provided to the induction coil 16 a current is caused to pass through the induction coil, causing an EM field to be generated. As mentioned above, the current supplied to the induction coil is an alternating (AC) current. This causes heat to be generated within the cartridge because, when the cartridge is located in the heating compartment 12, it is intended that the susceptor plates are arranged (substantially) parallel to the radius of the induction coil 16 as is shown in the figures, or at least have a length component parallel to the radius of the induction coil. Accordingly, when the AC current is supplied to the induction coil while the cartridge is located in the heating compartment, the positioning of the susceptor plates causes eddy currents to be induced in each plate due to coupling of the EM field generated by the induction coil to each susceptor plate. This causes heat to be generated in each plate by induction.

The plates of the cartridge 20 are in thermal communication with the vaporisable substance 22, in this example by direct or indirect contact between each susceptor plate and the vaporisable substance. This means that when the susceptor 24 is inductively heated by the induction coil 16 of the induction heating assembly 10, heat is transferred from the susceptor 24 to the vaporisable substance 22, to heat the vaporisable substance 22 causing it to volatilise producing a vapour.

When the temperature sensor 11 is in use, it monitors the temperature, step 102 by measuring temperature at its surface. Each temperature measurement is sent to the controller 13 in the form of an electrical signal. The controller is then able to process the electrical signal to obtain temperature information, step 103, related to heat generated from the susceptor. In this example, the temperature information includes one or more of the monitored temperature, the surface temperature of the cartridge 20 (which, as noted above, can be the monitored temperature) or the rate of change of temperature.

The controller 13 is also able to monitor the amount of power supplied by the power source 18 to the induction coil 16.

In this example the vapour generating device 1 also has a memory 28. Data is stored in the memory that represents a relationship between the temperature information, the amount of power supplied to the induction coil 16 and at least one condition of the cartridge. Accordingly, the memory holds the relationship. In this example, the at least one condition is one or more of an age of the cartridge 20, a type of the cartridge or whether a cartridge is present or not in the heating compartment 12.

In an alternative example the memory is located on an external device or is located in the cloud, by which we mean internet based computer storage and processing resources that are accessible on demand. In such as case, the vapour generating device has a memory accessor that is able to access and interact with the memory.

In use, the controller 13 is able to access the memory 28, step 104, to retrieve sufficient information to be able to determine, step 105, the at least one condition of the cartridge 20 based on the relationship by conducting processing using the temperature information and the amount of power supplied to the induction coil 16.

As an example of the relationship, for a cartridge containing tobacco, when heated the tobacco in the cartridge generates an aerosol. At the same time as the aerosol is created, the moisture level of the tobacco decreases due to the generation of the aerosol. Therefore, tobacco stored in an unused cartridge and tobacco stored in a used cartridge has different moisture levels, which may be determined by quantity of humectant (providing an aerosol former for example) and water. This has an impact on the rate of change in temperature as the cartridge is heated. For a used capsule, because of the reduced moisture level, such a cartridge heats up more quickly than an unused cartridge heated under the same conditions, so the rate of change of temperature is larger for a used cartridge than for an unused cartridge. Similarly, the amount of power required to heat a used cartridge to a particular temperature is less than for an unused cartridge. This of course also means that a used cartridge is able to be heated to a higher temperature than an unused cartridge when the same amount of power is supplied to the induction coil to provide heating.

A further example of the relationship is that the type of cartridge being heated is able to be determined. Due to differences between types of cartridge, such as differences in the composition of different cartridge types, supplying a particular amount of power to heat a cartridge heats different cartridge types to different temperatures. As such, if a surface temperature of a cartridge is within one temperature range, or is below a particular temperature threshold, the cartridge is able to be determined as one type of cartridge; if the surface temperature of the cartridge is within a second temperature range, or is between two temperature thresholds, then the cartridge is able to be determined as a second type of cartridge; if the surface temperature of the cartridge is within a third temperature range, is between two further temperature thresholds or is below or above a further temperature threshold, then the cartridge is able to be determined as a further type of cartridge.

Another example of the relationship is that whether a cartridge is present in the heating compartment is able to be determined. In this example, if power is supplied to the induction coil and the temperature remains below a temperature threshold, then no cartridge is present. On the other hand, if power is supplied to the induction coil and the temperature increases to or above the temperature threshold, then a cartridge is present. This aspect of the relationship exists because heat is generated by the susceptor in the cartridge, so if the cartridge is not present in the heating compartment, not heat will be produced since there will be no susceptor to generate heat, whereas if a cartridge is present there will be a susceptor to generate heat.

Of course, all three of the examples of the relationship described above are able to be determined at the same time. For example, if no cartridge is present, then the temperature able to be monitored will be below a first threshold temperature. If the temperature is between the first threshold temperature and a second threshold temperature of a higher temperature than the first threshold temperature, then the cartridge is an unused cartridge of a first type. If the temperature is between the second threshold temperature and a third threshold temperature of a higher temperature than the second threshold temperature, the cartridge is an unused cartridge of a second type. If the temperature is between the third threshold temperature and a fourth threshold of a temperature higher than the third threshold temperature, then the cartridge is an unused cartridge of third type of cartridge. If the temperature is above the fourth threshold temperature, then the cartridge is a used cartridge.

Once the at least one condition of the cartridge 20 is determined, the controller 13 selects the next action, step 106, to be carried out by the vapour generating device 1 based on the at least once condition. An example of the next action is to prohibit power being supplied to the induction coil 16 if the cartridge is used. This stops cartridges which are no longer suitable for heating from being used. Of course, the cartridge is able to be used more than a single use before it is determined as being a "used" cartridge. The amount of use a cartridge is exposed to before it is deemed to no longer be suitable is determined, for example, by the predetermined threshold temperature for used cartridges and when a cartridge reaches that temperature when heated from ambient temperature, the cartridge is considered to be "used". This allows cartridges to be used for a sustained period before being considered no longer suitable for heating.

Of course, if a cartridge 20 is determined as being unused, then the controller selects the next action as being supplying power to the induction coil 16 on demand.

In some examples, the vapour generating device 1 has an indicator or display (not shown) that indicates to the user the at least one condition of the cartridge 20 determined by the controller 13.

A user is able to use the device when they choose. As set out above, use of the device is achieved by the user drawing air through the passages of the device and out of the mouthpiece causing air (i.e. gas) to draw vapour generated in the heating compartment into the user's mouth. In some examples, the user drawing on the mouthpiece will act as a trigger event to start heating, and in other examples, another trigger is provided, such as a button push, to start heating.

Regardless of any trigger event, some uses by the user will be close together, for example over the period over which a conventional cigarette burns or a similar length of time, and some uses will be separated by significant periods of time, such as up to 15, 30, 60 minutes or more. These two categories of use can generally be separated into consecutive use in relation to the use pattern where the use is close together, and into non-consecutive use in relation to the use pattern where use is separated by a significant period of time. The consecutive use is use that generally falls into a single "session" of use of the vapour generating device with non-consecutive use being carried out over multiple sessions.

A session is generally intended to mean a time period during which the user may use the device within a short period of time. This is therefore a period during which the device should be available to provide vapour to the user in direct response to the user drawing on the mouthpiece. In some examples, each session may be delimited by a trigger event causing the session (and any associated heating) to start and to stop.

Within a session, for the vapour generating device described above, in some examples, heating is provided throughout a session (thereby including times when the user is drawing air through the device and when they are not drawing air through the device). On the other hand, between sessions no heating is provided meaning any response to the user being provided with vapour may be indirect, such as by a trigger instead of just by the user drawing on the device.

By having the device in an operational state (e.g. providing or ready to provide heating) during a session and in a non-operational state between sessions reduces power usage of the device. To increase this benefit, in some examples, the device is configured to "time-out" a session when the user has not drawn on the device for a predetermined time period. This allows further energy to be saved and reduces depletion of the cartridge vaporisable substance when the user is not drawing on the device.

Figure 4:
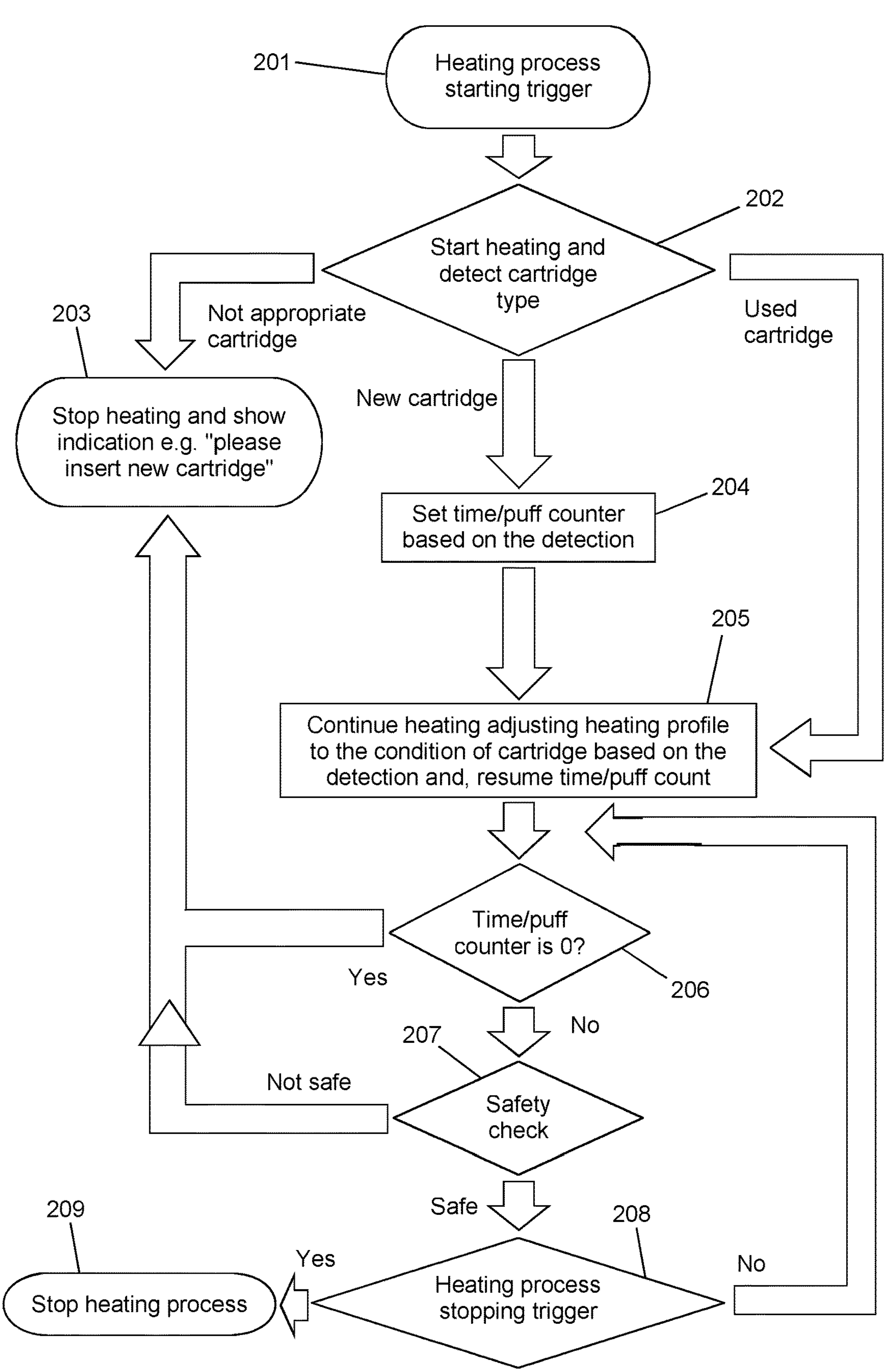
FIG. 4 shows a flow diagram of a further example process.

FIG. 4 shows an example process able to be carried out using the vapour generating device described above. When a user starts a session of use of the device, a heating process is started by a trigger event (step 201). The trigger event may for example be a push of a button by a user. In other examples, the trigger may be one of a number of events. One such event in some examples is the cartridge being removed from or a cartridge placed in the heating compartment of the vapour generating device.

In this case, in use, a cartridge is removed from the heating compartment of the vapour generating device by a user when it is no longer wanted. A cartridge is then inserted into the heating compartment by a user. To achieve this, the mouthpiece is removed from the rest of the body of the vapour generating device. This causes the heating compartment to be open and the cartridge to be accessible by the user. The cartridge is then pulled from the heating compartment by the user. A cartridge is then placed into the heating compartment by the user and the mouthpiece is re-attached to the rest of the body of the vapour generating device.

In embodiments where the mouthpiece is replaced by a cover (not shown) or a cover to the heating compartment is provided in addition to the mouthpiece at an alternate location to the mouthpiece, the cover being able to be articulated backward and forward to open and close the compartment, instead of removing the mouthpiece, the cartridge is removed from the chamber by opening the cover and the user pulling the cartridge through the opening at which the cover is located; said opening of course being in communication with the heating compartment. An alternate cartridge is then able to be introduced into the chamber by inserting it through said opening. The cover is then subsequently closed. In some alternative cases where the cartridge has a mouthpiece similar to a conventional cigarette the cover is kept open during the time the cartridge is located in the heating compartment.

As mentioned above, the trigger is able to be one of a number of events, which one such event being the removal/placing of a cartridge in/from the heating compartment. Taking this example, such a trigger in some examples is the opening/closing of the heating compartment, when this is detected (such as by a sensor in the vapour generating device), the controller is adapted to start a heating process as set out above.

The session may be a session using a cartridge that has previously been used or may be a cartridge that has not been used, such as a new cartridge, or a cartridge that is being used in the device for the first time. In the case the session is a session using a cartridge that has previously been used in the heating compartment of the device, the beginning of the session may be referred to as "restarting" the session. When the session is a session using a cartridge that has not previously been used in the heating compartment, and so is new to the device, then beginning of the session may be referred to as "starting" the session.

In the context of a session beginning, the terms "start" and "restart" are used interchangeably. As such, regardless of whether the session is being started or restarted, as mentioned above, a heating process is started. Using a process such as the process set out above in relation to FIG. 3, the type of the cartridge is detected (step 202). This allows a determination to be made as to whether the cartridge is a used cartridge, a new cartridge and/or is a cartridge of an inappropriate type for the vapour generating device.

If the cartridge type detected is not appropriate for the device for any reason, heating is stopped and the device provides an indication to the user (step 203). In this example, the indication may be provided in the form of a message on a display, the message, for example, reading "Please insert new cartridge".

When the cartridge type is detected as being an appropriate cartridge type (i.e. there is no determination the cartridge is an inappropriate, or not appropriate, type), and the cartridge is detected as being a new (i.e. unused) cartridge, the remaining heating time or number of remaining puffs for the cartridge is stored in a memory accessible by the controller based on the cartridge type detected (step 204). Should the memory contain previously stored information of this type, it is overwritten at this stage. This information may be inferred by the controller based on the cartridge being a new cartridge of an appropriate type for use with the vapor generating device, or may be determined using a process. Such a process is set out in more detail below.

Following this step, or when instead the cartridge is detected as being a used cartridge (and not detected as being an inappropriate type), heating is applied based on the amount of heating time remaining and/or number of puffs remaining (step 205).

In one example this involves the current type of the cartridge being ascertained by a memory accessible by the device being checked to determine the amount of time or number of puffs remaining for the cartridge present in the device. Once this determination has taken place, the amount of power provided for heating is capped to a predetermined amount based on the determination based on the amount of time or puffs remaining or still available for that cartridge. This then corresponds to the power amount to be applied for a particular type of cartridge, so a maximum power level is set to provide heating to a predetermined temperature.

An illustration of this determination can be seen from the hypothetical example of maximum power, target temperature and relative temperature ramp rate when the heating process is started/re-started shown in Table 1 below:

An illustration of this determination can be seen from the hypothetical example for cartridges previously present in the device of a relationship between session time or puff number, corresponding maximum power and the resulting target temperature when the hearting process is re-started shown in Table 1 below:

TABLE 1

| Cumulative heating time elapsed before re-start (e.g. minutes) or cumulative puffs taken before re-start | Maximum power applied on re-start (%) | Target temperature (° C.) |
|---|---|---|
| 1 | 15 | 130 |
| 2 | 10 | 130 |
| 3 | 7.5 | 130 |
| 4 | 5 | 130 |
| 5 | 2.5 | 130 |

For when the heating process is started/re-started, a further hypothetical example of a relationship between maximum power, target temperature and relative temperature ramp rate is shown in Table 2 below:

TABLE 1

| Maximum power applied on start/re-start (%) | Target temperature (° C.) | Temperature ramp rate on start/restart at known (low) power (° C./s) |
|---|---|---|
| 15 | 130 | 10 |
| 10 | 130 | 20 |
| 7.5 | 130 | 30 |
| 5 | 130 | 40 |
| 2.5 | 130 | 50 |

The relative temperature ramp rate of Table 2 corresponds to the rate of increase in temperature of the cartridge. This is the effect of the maximum, i.e. capped, power applied whilst still allowing the cartridge to arrive at the target temperature and/or maintaining the target temperature.

In relation to Table 2, a temperature ramp rate of 10 degrees centigrade per second (° C./s), for example, indicates there is a relatively large amount of humectant present in the cartridge compared to when the temperature ramp rate is 50° C./s. This means for a temperature ramp rate of 10° C./s, a suitable maximum power level to apply would be relatively large (e.g. 15% of the maximum power output of the heating device) compared to the suitable maximum power level when the temperature ramp rate is 50° C./s for example.

Considering Table 1, the cumulative amount of heating time previously elapsed can be seen to have an effect on the maximum power that will be applied since if the cumulative time is higher, the maximum power level is lower. However, this still allows the target temperature to be reached by the appropriate maximum power being set.

With the examples set out in Tables 1 and 2, it may be possible to determine the maximum power that is to be applied. For the example of Table 1, this may be achieved by monitoring the temperature ramp rate at a known power and determining the maximum power level to apply based on the value(s) read from memory compared to a look-up table or database with similar values to that of Table 2. For the example of Table 1, determining the maximum power may be achieved by reading the cumulative time elapsed or cumulative number of puffs (or time or number of puffs remaining) from memory and determining the maximum power level to apply based on the value(s) read from memory compared to a look-up table or database with similar values to that of Table 1.

This process corresponds to the process set out in FIG. 3, with the selection of the next action based on the determined at least one condition in step 106 corresponding to the next action being setting of maximum power.

These examples is also the process that may be applied to determine the number of puffs remaining or total amount of heating time remaining for a new cartridge.

As the session continues, the device moves from the step of determining what maximum power to applied to a normal operating heating mode, the normal operating heating mode corresponding in some embodiments to the second power supply mode described above. At this time, the determined maximum power level suitable for the cartridge is applied. The maximum power level to provide heating may then be able to be adjusted based on the condition of the cartridge as it changes if necessary. This adjustment of the heating profile is based on, for example as explained above, the remaining time or remaining number of puffs available for the cartridge, and is achieved by a memory accessible by the device being checked to determine the appropriate power amount to be applied to a cartridge with that amount of usage time/number of remaining puffs.

Use of the cartridge by exposure to heating and by gas being drawn over the cartridge through use of the vapour generating device by the user causes the remaining amount of heating time and remaining number of puffs to decrease. In this example, this decrease is monitored so the remaining amount of heating time and remaining number of puffs is known.

As such, while the normal operating heating mode continues, the time remaining for the cartridge to be heated is monitor and/or the number of puffs for the cartridge is monitored while heating is still being applied. A check is carried out to ascertain if the remaining time or remaining puffs has reached zero (step 206). If the remaining time or remaining puffs has reached zero, then heating is stopped and the device provides an indication to the user (step 203). The indication to the user may be the same as when the cartridge is detected as not being the appropriate type for the device.

If the remaining time or puff count has not reached zero, a safety check is performed (step 207). This is carried out to avoid a change in cartridge not being detected and an empty cartridge being placed in the device in place of, for example, a partially used cartridge. In some examples this involves monitoring the temperature of the cartridge using the temperature sensor and the controller determining if the temperature indicated by the data output from the temperature sensor corresponds to an expected temperature of the cartridge of the type (for example age) the device understands from the process set out above to be present, or a higher than expected temperature.

The expectation of the temperature the cartridge should be may correspond to a stored temperature range in which cartridges suitable for the device are designed to be used in. If the temperature is higher than expected, i.e. it is higher than a predetermined threshold temperature (the top of the stored temperature range for example), this is an indication the cartridge is overheating and may become damaged. As such, if this is detected in the safety check, heating is stopped and the device provides an indication to the user (step 203). The indication to the user may be the same as when the cartridge is detected as not being the appropriate type for the device.

If the cartridge is considered safe to continue using at the safety check, a further check is carried out to ascertain if a stop trigger for the heating process has been received (step 208). In some examples, the stop trigger is provided by the user pushing a button, which may be the same button as the button that provides the start trigger. If the stop trigger is received then heating is stopped (step 209). If no stop trigger has been received, then the process proceeds in a cycle by returning to the check of whether the remaining time or puff count is zero in step 206.

When heating is stopped, the remaining amount of heating time and/or the remaining number of puffs is stored in the memory to allow it to be used on re-start of a new session if the current cartridge is not replaced. Following heating being stopped, the whole process may be restarted when the next start trigger is received.

As set out above, each cartridge used with the vapour generating device described above contains a volume of vaporisable substance. This volume is at its largest when the cartridge is new. The volume then decreases as the vaporisable substance in the cartridge is depleted through use of the cartridge. In some examples, the cartridge is determined by the controller as an inappropriate type of cartridge when the amount of vaporisable substance is inferred as being below a predetermined threshold. This threshold may relate to an amount of puffs remaining or an amount of heating time remaining, or the converse parameters of the amount of puffs experienced by the cartridge or cumulative amount of time for which the cartridge has been heated. In some examples, the threshold is between 3 and 30 puffs and/or between 5 and 20 minutes cumulative heating time. By "cumulative heating time" it is intended to mean the total amount of time over which heating has been applied, which may extend over a number of sessions depending on how the cartridge and vapour generating device is used.

The invention claimed is:

1. A heating assembly for a vapour generating device, the heating assembly comprising:

a heating device configured to heat a body comprising a vaporisable substance, wherein the heating assembly is configured to supply power to the heating device to heat the body to volatilise the vaporisable substance, a quantity of the vaporisable substance in the body thereby reducing on heating;

a passage configured to allow gas to be drawn over the body; and a controller configured to:

monitor and store vaporisable substance quantity information of the quantity of the vaporisable substance in the body by determining an amount of previous usage of the body based on stored time the body has been heated for and/or a stored number of times gas has been drawn over the body during heating, set a maximum power level suppliable to the heating device based on the stored vaporisable substance quantity information, provide the set maximum power level to the heating device to heat the body, determine a water content of the body based on a rate of increase of a surface temperature of the body, and based on said determination of the water content, provide a reduced power level to the heating device to heat the body at a reduced temperature for a waiting period to decrease the water content.

2. The heating assembly according to claim 1, wherein the controller is further arranged to set a maximum amount of power suppliable to the heating device based on the stored vaporisable substance quantity information and/or a stored relationship between temperature information determinable from a monitored temperature during heating and an amount of power supplied to the heating device or a profile of power supplied to the heating device.

3. The heating assembly according to claim 2, wherein the controller is arranged, based on the quantity of the vaporisable substance in the body, to set the maximum amount of power suppliable to the heating device lower for a body with less vaporisable substance than a body with more vaporisable substance.

4. The heating assembly according to claim 1, wherein the controller is further configured to replace the stored vaporisable substance quantity information with new vaporisable substance quantity information when the controller determines the body is previously unused.

5. The heating assembly according to claim 1, wherein the controller is further configured to prohibit heating of the body when the vaporisable substance quantity in the body is below a threshold.

6. The heating assembly according to claim 5, wherein the threshold below which the controller is further configured to prohibit heating of the body is when gas has been drawn over the body between 3 and 30 times or the body has cumulatively been heated for between 5 and 20 minutes.

7. The heating assembly according to claim 1, wherein the vaporisable substance is solid.

8. The heating assembly according to claim 1, wherein the controller is configured to apply heating when gas is being drawn over the body and when no gas is being drawn over the body.

9. The heating assembly according to claim 1, further comprising a temperature sensor configured to monitor a temperature relating to heating at the body.

10. The heating assembly according to claim 9, wherein the controller is configured to receive temperature information from the temperature sensor and to stop heating if a temperature of the body exceeds a predetermined threshold.

11. The heating assembly according to claim 9, wherein the controller is configured to determine if the body is previously unused based on a stored relationship between temperature information determinable from a monitored temperature during heating, age of the body, and an amount of power supplied to the heating device or a profile of power supplied to the heating device.

12. The heating assembly according to claim 11, wherein the controller is configured to determine if the body is a previously unused body on detection of the body being placed for heating by the heating device.

13. The heating assembly according to claim 1, wherein the controller is configured to determine if the body is a body unsuitable for use with the assembly, is a suitable used body, or is a suitable unused body, wherein after the determination, the controller is further configured to:

if the body is determined as an unsuitable body, prohibit heating by the heating device, if the body is determined as a suitable unused body, initiate heating by the heating device and replace the stored vaporisable substance quantity information with new vaporisable substance quantity information, or if the body is determined as a suitable used body, initiate heating by the heating device based on the stored vaporisable substance quantity information.

14. A method of heating a body, the body comprising a vaporisable substance, the vaporisable substance volatilising on heating, the method comprising:

determining, with a controller, an amount of previous usage of the body based on stored time the body has been heated for and/or a stored number of times gas has been drawn over the body during heating;

setting, with the controller, a maximum power level suppliable to a heating device based on a stored vaporisable substance quantity in the body; and heating the body, with the heating device, the heating device being provided the set maximum power level, determining, by the controller, a water content of the body based on a rate of increase of a surface temperature of the body; and based on said determination of the water content, provide by the controller, a reduced power level to the heating device to heat the body at a reduced temperature for a waiting period to decrease the water content.

15. A vapour generating device comprising:

the heating assembly according to claim 1;

a body containing a vaporisable substance, the body being heatable by the heating assembly; and an air inlet and an air outlet providing the passage therebetween arranged in use to allow gas to pass over the body during heating to provide air to a heating compartment.

* * * * *